United States Patent [19]

Rzeszotarski et al.

[11] Patent Number: 4,843,074
[45] Date of Patent: Jun. 27, 1989

[54] 1-AZABICYCLO[2.2.2]OCTAN-3-YL 2-ARYL-3-AZACYCLO-2-HYDROXYPROPIONATES AND THEIR QUATERNARY SALTS

[75] Inventors: Waclaw J. Rzeszotarski, Millersville; Vicki H. Audia; Moshe Weitzberg, both of Baltimore, all of Md.

[73] Assignee: Marion Laboratories, Inc., Kansas City, Mo.

[21] Appl. No.: 194,905

[22] Filed: May 17, 1988

[51] Int. Cl.$^4$ .................. A61K 31/435; A61K 31/54; A61K 31/535; C07D 453/00

[52] U.S. Cl. .......................... 514/228.2; 514/233.2; 514/253; 514/278; 514/305; 544/58.6; 544/127; 544/362; 546/16; 546/137

[58] Field of Search .................. 544/58.6, 127, 362; 546/16, 137; 514/228.2, 233.2, 253, 278, 305

[56] References Cited

U.S. PATENT DOCUMENTS 4,644,003  2/1987  Rzeszotarski et al. .............. 546/137

Primary Examiner—Richard L. Raymond
Attorney, Agent, or Firm—Dewey, Ballantine Bushby, Palmer & Wood

[57] ABSTRACT

Novel 1-azabicyclo[2.2.2]octan-3-yl 2-aryl-3-azacyclo-2-hydroxypropionates and their quaternary salts and their use as antimuscarinic agents having antisecretory activity selective for the gastrointestinal tract are disclosed. The compounds have the formula:

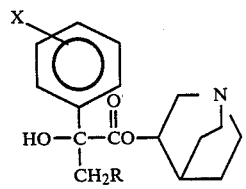

wherein:
X = H, halogen, lower alkyl, lower alkoxy, hydroxy, and
R = morpholinyl, thiomorpholinyl, piperidinyl, 1,4-dioxa-8-azaspiro[4.5]decanyl, 4-(2,6-dimethylmorpholinyl), 4-ketopiperidinyl, 4-hydroxypiperidinyl, 4-substituted piperazinyl (wherein the substituent is lower alkyl, hydroxyalkyl, acetoxyalkyl, or acyl).

Also disclosed are pharmaceutical compositions for treatment of irritable bowel syndrome and methods for using such compounds.

7 Claims, No Drawings

1-AZABICYCLO[2.2.2]OCTAN-3-YL 2-ARYL-3-AZACYCLO-2-HYDROXYPROPIONATES AND THEIR QUATERNARY SALTS

BACKGROUND OF INVENTION (a) Field of Invention

This invention relates to novel 1-azabicyclo[2.2.2]octan-3-yl 2-aryl-3-azacyclo-2-hydroxypropionates and their quaternary salts and their use as antimuscarinic agents having antisecretory activity selective for the gastrointestinal tract.

(b) State of the Art

Blockade of the action of acetylcholine at muscarinic cholinergic receptors in various tissues produces antispasmodic, antisecretory and mydriatic effects. As a result, such compounds have a broad range of therapeutic applications, notably as antispasmodics, as an adjunct in the management of peptic ulcer, as adjuvants in the management of functional disorders of the bowel, such as irritable colon, spastic colitis, ulcerative colitis, diverticulitis, and irritable bowel syndrome.

Unfortunately, many of these agents lack specificity; that is, they produce side effects, notably, central nervous system symptoms such as dizziness and hallucinations [B. V. Rama Sastry, in "Burger's Medicinal Chemistry", Edited by M. E. Wolff, 4th Edition, Part III, Wiley-Interscience, New York, 1980, pp. 361-411; S. N. Pradhan, in "Pharmacology in Medicine: Principles and Practice", Edited by S. N. Pradhan, R. P. Maickel and S. N. Dutta, SP Press, Bethesda, Md., 1986, pp. 138-165)].

The novel 1-azabicyclo[2.2.2]octan-3-yl 2-aryl-3-azacyclo-2-hydroxypropionates and their quaternary salts described herein are potent antimuscarinic agents with a high degree of selectivity for the gastrointestinal tract as evidenced by their ability to displace muscarinic ([$^3$H]QNB) ligands from their tissue binding sites, decrease colonic motility and to inhibit carbachol-induced diarrhea in animals. The polar nature of these compound limits their access to the central nervous system. These actions indicate usefulness of these substances as antispasmodics and in the treatment of irritable bowel syndrome.

SUMMARY OF THE INVENTION

The invention provides novel compounds of formula:

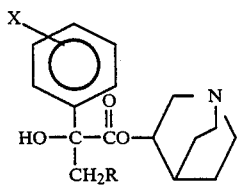

and their quaternary salts with lower alkyl halides, wherein:

X=H, halogen, lower alkyl, lower alkoxy, hydroxy, and

R=morpholinyl, thiomorpholinyl, piperidinyl, 1,4-dioxa-8-azaspiro[4.5]decanyl, 4-(2,6-dimethylmorpholinyl), 4-ketopiperidinyl, 4-hydroxypiperidinyl, 4-substituted piperazinyl (wherein the substituent is lower alkyl, hydroxyalkyl, acetoxyalkyl or acyl).

Lower alkyl and lower alkoxy as used in this application refer to groups having one to six carbons. This invention also provides pharmaceutical compositions for treatment of irritable bowel syndrome and methods for using such compounds.

DETAILED DESCRIPTION OF THE INVENTION

The compounds of the invention are novel 1-azabicyclo[2.2.2]octan-3-yl 2-aryl-3-azabicyclo-2-hydroxypropionates of the above formula and their salts. The compounds are potent antimuscarinic agents with selectivity toward the gastrointestinal tract, making them useful as antispasmodics and in the treatment of irritable bowel syndrome. The invention thus includes pharmaceutical compositions intended for such uses which comprise an effective amount of the compounds of the invention and a pharmaceutically acceptable carrier. The invention also includes methods of using such compositions as antispasmodics and to treat irritable bowel syndrome, wherein an effective amount of the composition is administered to a host suffering from the disorder.

The preferred compounds of the invention are: 1-azabicyclo[2.2.2]octan-3-yl 2-hydroxy-3-(4-morpholinyl)-2-phenylpropionate, 1-azabicyclo[2.2.2]octan-3-yl 2-hydroxy-2-phenyl-3-(4-thiomorpholinyl)propionate, 1-methyl-1-azabicyclo[2.2.2]octan-3-yl 2-hydroxy-3-(4-morpholinyl)-2-phenylpropionate iodide and 1-methyl-1-azabicyclo[2.2.2]octan-3-yl 2-hydroxy-2-phenyl-3-(4-thiomorpholinyl)propionate iodide.

The lower alkyl halide quaternary salts of the foregoing compounds are included within the invention. The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicyclic methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. To the extent the compounds of the invention may exist as optical isomers, both isomers and the racemic mixture are to be understood to be included in the invention. In addition, all possible other isomeric forms of the compounds of the invention are within the ambit of this invention.

The compounds of this invention may be administered orally or parenterally in conventional dosage unit forms such as tablets, capsules, injectables, aerosols, or the like, by incorporating the appropriate dose of a compound of the indicated formula with carriers according to accepted pharmaceutical practices.

Preferably a compound or an acid addition salt thereof is administered orally to an animal organism in a tablet or capsule comprising an amount sufficient to produce the desired activity. Each dosage unit will contain the active ingredient in an amount of about 1 mg. to about 40 mg., preferably from about 3 mg. to about 20 mg. Advantageously equal doses will be administered 2 to 4 times daily with the daily dosage regimen being about 0.1 mg. to about 160 mg., preferably from about 6 mg. to about 80 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous or nonaqueous liquid suspension.

The compounds of the invention can be prepared from the appropriately substituted ethyl α-phenylglycidate and the requisite azacyclo compound followed by transesterification of the ethyl ester with 1-azabicyclo[2.2.2]octan-3-ol. Appropriately substituted ethyl phenylglycidates can be obtained by literature methods [G. R. Ames and W. Davey, J. Chem. Soc., 1958, 1794–1799; J. A. Fee et al., Biochemistry, 13, 2533–2538 (1974)]; for example, by condensation of an alkyl arylacetate with diethyl oxalate followed by further condensation with formaldehyde and decarboxylation followed by m-chloroperbenzoic acid (MCPBA) oxidation of the intermediate.

The following examples are illustrative of the invention. Temperature is expressed as degrees Celsius; NMR signals are given as ppm downfield from an internal standard of Me$_4$Si.

EXAMPLES

Example I

Ethyl atropate.

A solution of diethyl oxalate (75 g, 513 mmole) and ethyl phenylacetate (108 g, 658 mmol) in 300 mL of dry toluene was slowly charged with solid sodium ethoxide (33.3 g, 489 mmol). A mild exothermic reaction was observed and the reaction mixture turned orange. Precipitation of the salt started within 1 hour and the reaction was left at room temperature overnight. The salt was filtered and washed thoroughly with dry ether. The solid was suspended in 200 mL of ether then acidified to pH2 with 5% aqueous hydrochloric acid. The aqueous layer was separated followed by additional extraction with ether (2×50 mL). The combined etheral solution was successively washed with a saturated solution of sodium bicarbonate (50 mL), water (2×50mL) and brine (50 mL), dried over magnesium sulfate and evaporated in vacuum at room temperature (to prevent possible decarboxylation). The resulting yellow oil was charged with water (250 mL) and formaldehyde (81 mL, 37% aqueous solution, 1 mole) and then it was cooled to 0° C. The resulting mixture was charged, very slowly, with potassium carbonate (72 g, 521 mmol), over 30 minutes. The temperature in the reaction flask was not allowed to exceed 15° C. The reaction mixture was stirred at room temperature for an additional two hours. The aqueous solution was extracted with ether (2×50 mL) and the combined ethereal solution was washed with water (2× 50 mL) and brine (50 mL), dried over magnesium sulfate and evaporated. The resulting yellow oil was purified by Kugelrohr distillation (80°–85° C., 0.5 mmHg) to yield 82.3 g (91%). 300MHz $^1$H NMR (CDCl$_3$)δ7.46–7.31 (m,5 H), 6.37 (d, J=1.17 Hz, 1H), 5.91 (d, J=1.17 Hz, 1H), 4.31 (q, J=7.15 Hz, 2 H), 1.35 (t, J=7.15 Hz, 3 H). IR (neat)2995, 1740, 1610, 1500, 1450, 1405, 1370, 1310, 1200 cm$^{-1}$.

Ethyl 2-Phenyl-2,3-epoxypropionate.

A cooled (0° C.) solution of ethyl atropate (17.5 g, 99.3 mmol) in 300 mL of methylene chloride was slowly charged with m-chloroperbenzoic acid (40.45 g, 119.2 mmol, 85%). The solution was left at room temperature for three days. The resulting slurry was filtered and the solid was washed with methylene chloride (2×30 mL) at 0° C. The combined organic solvent was treated with 1:1 solution of 5% sodium bicarbonate and 3% sodium thiosulfate (3×50 mL), followed by successive washings with water (2×30 mL) and brine (30 mL), then dried over magnesium sulfate and evaporated. The crude yield of the ethyl 2-phenyl-2,3epoxypropionate, which showed at least 90% purity by NMR and was clean enough to be carried on to the next step, was 17.9 g (94%). A pure colorless product was obtained by Kugelrohr distillation of the oil in the presence of solid potassium carbonate to prevent polymerization (100° C., 0.3 mmHg) and yielded 17.1 g (89.6%). 300 MHz$^1$H NMR (CDCl$_3$) δ7.51–7.33 (m, 5 H), 4.23 (q, J=7.18 Hz, 2 H), 3.40 (d, J=7.11 Hz, 1H), 2.94 (d, J=7.11 Hz, 1 H), 1.26 (t, J=7.18 Hz, 3 H). IR (neat) 3000, 1780, 1450, 1370, 1300, 1205 cm$^{-1}$.

Ethyl 2-Hydroxy-2-phenyl-3-(4-morpholinyl)propionate.

Ethyl alpha-phenylglycidate (4.96 g, 25.8 mmol) was dissolved in 50 mL of ethanol. To the solution was added morpholine (6.79 g, 78.0 mmol) and the solution was refluxed for 18 hours. The solution was cooled and ether added. The mixture was washed twice with a saturated sodium chloride solution, dried over sodium sulfate, and evaporated to dryness to afford a yellow oil. The product was purified by flash column chromatography (silica, chloroform:triethylamine, 100:2)) to afford a pale yellow oil (4.56 g, 63.2%). IR (neat) 3495, 1730, 1450, 1232 cm$^{-1}$. $^1$H NMR (CDCl$_3$)δ1.2 (t, 3 H), 2.7 (d, 1 H, J=13.4 Hz), 2.8 (m, 2 H), 3.3 (d, 1 H, J=13.4 Hz), 3.6 (m, 4 H), 4.2 (q, 2 H), 4.6 (bs, 1 H), 7.3–7.4 (m, 5 H).

1-Azabicyclo [2.2.2]octan-3-yl 2-Hydroxy-3-(4-morpholinyl)-2-phenylpropionate.

A solution of 3-quinuclidinol (5.78 g, 45.4 mmol) in benzene (150 mL) was refluxed utilizing a Dean-Stark distillation apparatus for one hour to remove water present. The solution was cooled, about 1 g of sodium pellets was added and the solution refluxed as above for one hour. The solution was allowed to cool slightly and then was transferred to a solution of the above propionate (4.24 g, 15.2 mmol) in benzene (150 mL) which had been refluxed as above to remove water present. The resulting mixture was then refluxed for 18 hours utilizing a Dean-Stark apparatus. The mixture was cooled and evaporated to dryness. The residue was washed with ethyl acetate and filtered. The ethyl acetate solution was washed with water followed by a saturated sodium chloride solution, dried over sodium sulfate, and evaporated to dryness to afford an orange oil. The product was purified by flash column chromatography (silica, chloroform:triethylamine 100:2) followed by chloroform:methanol:triethylamine, 99:1:2) and passing the product obtained through a plug of Florisil. This afforded the product as a pale yellow solid (3.76 g, 68.4%), mp 92°–93° C. IR (KBr) 3379, 1720, 1450 cm$^{-1}$. TLC (RP-C18, methanol:0.5M ammonium acetate, 8:2)

Rf=0.63. NMR (CDCl$_3$) δ1.3–2.0 (m, 5 H), 2.5–2.9 (m, 10 H), 2.7 (d, 1 H), 3.2 (m, 1 H), 3.3 (d, 1 H), 3.7 (m, 4 H), 4.8 (bs, 1 H), 4.9 (m, 1 H), 7.2–7.6 (m, 5H). Anal. calcd. for C$_{20}$H$_{28}$N$_2$O$_4$.2H$_2$O: C, 65.98; H, 7.86; N, 7.69. Found: C, 66.01, 65.93; H, 7.73, 7.78; N. 7.61.

Example II

Ethyl 2-Hydroxy-2-phenyl-3-(4-thiomorpholinyl)-propionate.

Ethyl alpha-phenylglycidate (6.34 g, 33.0 mmol) was dissolved in 50 mL of ethanol. To the solution was added thiomorpholine (10.26 g, 99.4 mmol) and the solution was refluxed for 18 hours. The solution was cooled and ether added. The mixture was washed twice with a saturated sodium chloride solution, dried over sodium sulfate, and evaporated to dryness to afford a yellow oil. The product was purified by flash column chromatography (silica, chloroform:triethylamine, 100:2)) to afford a pale yellow oil (7.79 g, 80.0%). NMR (CDCl$_3$)δ1.3 (t, 3 H), 2.6 (m, 4 H), 2.7 (d, 1 H), 2.9 (m, 4 H), 3.3 (d, 1 H), 4.2 (q, 2 H), 4.6 (s, 1 H), 7.3–7.6 (m, 5 H).

1-Azabicyclo [2.2.2]octan-3-yl 2-Hydroxy-2-phenyl-3-(4-thiomorpholinyl)propionate.

A solution of 3-quinuclidinol (7.13 g, 57.5 mmol) in benzene (150 mL) was refluxed utilizing a Dean-Stark distillation apparatus for one hour to remove water present. The solution was cooled, about 1 g of sodium pellets was added and the solution refluxed as above for one hour. The solution was allowed to cool slightly and then was transferred to a solution of the above propionate (5.31 g, 18.0 mmol) in benzene (150 mL1 which had been refluxed as above to remove water present. The resulting mixture was then refluxed for 18 hours utilizing a Dean-Stark apparatus. The mixture was cooled and evaporated to dryness. The residue was washed with ethyl acetate and filtered. The ethyl acetate solution was washed with water followed by a saturated sodium chloride solution, dried over sodium sulfate, and evaporated to dryness to afford an orange solid. The solid was washed with petroleum ether and filtered to remove starting ester. The solid was then purified by flash column chromatography (silica, chloroform:triethylamine, 100:2 followed by chloroform:methanol:triethylamine, 99:1:2) and passing the product obtained through a plug of Florisil. This afforded the product as a white solid (4.43 g, 65.6%), mp 130° C., IR (KBr) 3443, 1736 cm$^{-1}$. TLC (RP-C18, methanol:0.5M ammonium acetate, 8:2) Rf=0.48. NMR (CDCl$_3$) 1.2–2.0 (m, 5 H), 2.7–3.1 (m, 13 H), 2.9 (d, 1 H), 3.2 (m, 1 H), 3.4 (d, 1 H), 4.5 (bs, 1 H), 4.8 (m, 1 H), 7.2–7.7 (m, 5H). Anal. calcd. for C$_{20}$H$_{28}$N$_2$O$_3$S.H$_2$O: C, 60.88; H, 7.66; N, 7.10; S, 8.13. Found: C, 60.63, 60.55; H, 7.18, 7.20; N, 7.09, 7.04; S, 8.05.

Also prepared bythe general method described in Examples I and II were: 1-azabicyclo[2.2.2]octan-3-yl 2-hydroxy-2-phenyl-3-piperidinylpropionate dihydrochloride sesquihydrate (mp 142°–147° C.), 1-azabicyclo[2.2.2]octan-3-yl 2-hydroxy-2-phenyl-3-(4-methylpiperazinyl)propionate trihydrochloride (mp 198°–205° C.), 1-azabicyclo[2.2.2]octan-3-yl-2-hydroxy-2-phenyl-3-pyrrolidinylpropionate dihydrochloride (mp 248°–251° C. dec), 1-azabicyclo[2.2.2]octan-3-yl-3-(1,4-dioxa-8-azaspiro[4.5]decanyl)-2-hydroxy-2-phenylpropionate (mp 43°–47° C.), 1-azabicyclo[2.2.2]octan-3-yl 2-hydroxy-2-phenyl-3[4-(2,6-dimethylmorpholinyl)]propionate dihydrochloride hemihydrate (mp 205°–210° C. dec), and 1-azabicyclo[2.2.2]octan-3-yl 2-hydroxy-2-phenyl-3-piperazinylpropionate trihydrochloride hydrate (mp 200°–201° C.).

Example III

1-Methyl-1-azabicyclo[2.2.2]octan-3-yl 2-Hydroxy-3-(4-morpholinyl)-2-phenylpropionate Iodide.

The free base of 1-azabicyclo[2.2.2]octan-3-yl-2-hydroxy-3-(4-morpholinyl)-2-phenylpropionate (0.79 g, 2.2 mmol) was dissolved in 55 mL of ether and methyl iodide (0.32 g, 2.2 mmol) was then added. The solution was stirred at room temperature for 24 hours and then the solvent was removed under vacuum to afford a yellow solid. The solid was washed with ether and the product recrystallized from ether/ethanol to afford yellow crystals (0.95 g, 86.4%). Mp, 130° C., (dec). NMR (CDCl$_3$)δ1.9 (m, 2 H), 2.1 (m, 2 H), 2.5 (d, 1 H), 2.6 (m, 4 H), 2.9 (t, 1 H), 3.2–4.0 (m, 14 H), 4.3 (m, 1 H), 5.2 (bs, 1 H), 7.3–7.5 (m, 3 H), 7.6 (m, 1 H), 7.7 (m, 1 H). IR (KBr) 3394, 1733, 1116 cm$^{-1}$. TLC (RP-C18, methanol:0.5M ammonium acetate, 8:2) Rf=0.72. Anal. calcd. for C$_{21}$H$_{31}$IN$_2$O$_4$: C, 50.21; H, 6.22; N, 5.58; I, 25.26. Found: C, 50.01; H, 6.28; N, 5.49; I, 25.19.

Quaternary salts of the other compounds outlined in Examples I to III are prepared in a similar fashion.

Example IV

[$^3$H]QNB Binding to Particulate Fraction of Rat Ileum.

All compounds were tested for potency to inhibit the specific binding of [$^3$H]QNB to a particulate fraction of rat ileum. Fresh rat ileum was cleaned of connective tissue and luminal contents, homogenized (Polytron setting #5.5 for 15 seconds) in 10×volume (w/v) of 50 mM Tris HCl (pH 7.7 at room temperature) and centrifuged at 20,000 rpm for 10 minutes at 4° C. The tissue pellet was washed twice by resuspension and centrifugation as above and suspended in 50 mM Tris HCl to a concentration of 6 mg/mL.

Inhibition of the specific binding of [$^3$H]QNB to a particulate preparation of rat ileum was performed using triplicate incubations in a total assay volume of 2 mL containing 0.2 nM [$^3$H]QNB (NEN; S.A.=35.2 Ci/mmole), 6 mg tissue, 50 mM Tris HCl (pH 7.7 at room temperature) and 10 concentrations of the test compounds. Nonspecific binding was defined by 10$^{-6}$ M atropine. Following a 2 hour incubation at room temperature, the binding reaction was stopped by vacuum filtration (Whatman GF/B filters). Samples were counted (Beckmann Ready Safe scintillation fluid) in a Beckmann LSM-11 counter. The apparent Ki affinity constant was calculated from the following equation.

$$Ki = \frac{IC_{50} \text{ (concentration which elicits 50\% inhibition)}}{1 + \frac{(L) \text{ Ligand Concentration)}}{kd \text{ (dissociation fraction)}}}$$

The apparent Kd for [$^3$H]QNB in this tissue preparation was calculated from 2 separate saturation experiments and an average value of 0.2 nM was obtained.

Inhibition of Colonic Motility in Anesthetized Rats.

Male rats (300–450 g), food deprived 24–48 hours prior to experimentation, are anesthetized i.p. with urethane (1.5 g/kg). Femoral and jugular veins are cannulated with PE-50 containing heparinized saline. The trachea are cannulated with 15-gauge Intramedic luer stub adapters. A 6–8 cm piece of PE-350 is inserted into the rectum of each animal, and colons are flushed with 10 mL of saline. A 3-F ultraminiature Millar pressure transducer is inserted 5 cm into each rectum and taped down to the rat heating board.

Animals are given 30 minutes to recover and baseline colonic pressures are set to zero prior to dosing. Carbachol doses (10 µg/225) g) are administered as a bolus through the jugular veins at 20 minute intervals, flushing each dose with 0.5 mL of heparinized saline. The first three (or more, if necessary) responses serve as "controls". After controls are obtained, the drugs are administered through the femoral veins, starting with the lowest dose (0.001 or 0.0001 mg/kg) and proceeding to the highest dose (10.0 or 1.0 mg/kg) 5 minutes prior to each subsequent carbachol dose, flushing each with 0.5 mL of heparinized saline. The maximum volume injected per animal is 6 mL.

Bolus responses are integrated by the Gould recorder. Control reponses are averaged and each carbachol response following a drug dose is calculated as the percent inhibition of the average control. After obtaining an "n" of 6-8 animals per drug, $EC_{50}$s are determined by plotting percent inhibition per dose for each animal on semi-log paper and averaging the 50% values.

Inhibition of Carbachol-Stimulated Chloride Secretion.

Male Hartley pigs weighing 200-400 g were maintained on a standard laboratory diet with free access to food and water prior to sacrifice by decapitation. About 15 cm of proximal ileum was removed and stripped of its underlying longitudinal muscle by blunt dissection. Four adjacent tissues were then mounted as a flat sheet between two lucite half-chambers (exposed area=0.64 cm$^2$) and baths on both sides by a physiological salt solution circulated by gas lift, and maintained at 37° C. by water jacketed reservoirs. The solution was gassed continuously with 5% $CO_2$ in $O_2$ and maintained at a pH of 7.4. The ionic composition in mmol/L was: 142,Na+; 5.0, K+; 123.7, Cl−; 25, $HCO_3$−; 1.65, $HPO_4$−; 0.3, $H_2PO_4$−.

Electrical measurements were monitored with an automatic voltage clamp (World Precision Instruments, model DVC-1000). Two calomel electrodes with 4% agar Krebs Bicarbonate Ringer bridges were used to measure the transepitheleal potential difference (PD) across the isolated mucosa. The spontaneous tissue PD was short-circuited throughout the experiment and the clamp current (Isc) was passed with silver/silver chloride electrodes located on each side of the tissue. The Isc was recorded on a Gould strip chart recorder.

The tissues were allowed to stabilize 30 minutes prior to addition of drugs. Cumulative additions of carbachol (0.1-100 µM) were made to both the mucosal and serosal sides of the tissue. In test tissues, test compounds were added to both serosal and mucosal sides 5 minutes prior to carbachol. The dose ratio (DR) was calculated at the $EC_{50}$ for the aganist in the presence of the antagonist divided by the $EC_{50}$ for the control. The Kb (dissociation constant) was calculated from the following equation:

$$Kb = \frac{Antagonist}{DR - 1}$$

Inhibition of Carbachol-Induced Diarrhea in Mice

Male CF1 mice (20-30 g) were food deprived for 24 hours prior to the experiments. Drugs were prepared in isotonic saline or an appropriate vehicle at varying concentrations and were administered intraperitoneally. Control animals were given vehicles without any test drug. Carbachol was given intraperitoneally in all cases 30 minutes after i.p. administration of test drug. Mice were placed in individual cages containing racks and paper liners with free access to water. Mice were observed after 30 minutes, 60 minutes and 180 minutes and graded for presence or absence of diarrhea. The grading system consisted of positive (+), negative (−) and (±) based on consistency and liquid staining. The $ED_{50}$ (effective dose in 50% of population) was calculated for each test drug using the method of Litchfield-Wilcoxin.

The results of all tests are set forth in the table below.

As indicated by the ability of the novel compounds of this invention to displace [$^3$H]QNB from its binding sites, to decrease colonic motility in anesthetized rats, to inhibit carbachol-stimulated cloride secretion and to block carbachol-induced diarrhea in mice, potential utility in the treatment of irritable bowel syndrome is strongly indicated.

| Compd. | [$^3$H]QNB Binding, Kb,nM | Colonic Motility Anesth. Rat, i.v., $IC_{50}$ (mg/kg) | Inhn. Carbachol-Stim. Cl- Sec. Kb,nM | Antag. Carbachol-ind. diarrhea, mice ip, $ED_{50}$, mg/lg |
|---|---|---|---|---|
| Dicyclomine | 46 | 0.33 (est.) | 57.0 | 0.65 |
| 1-Azabicyclo[2.2.2]octan-3-yl 2-Hydroxy-2-phenyl-3-piperidinylpropionate dihydrochloride sesquihydrate | 8277. | — | — | — |
| 1-Azabicyclo[2.2.2]octan-3-yl 2-Hydroxy-2-phenyl-3-(4-methyl-piperazinyl)propionate trihydrochloride | 9185. | — | — | — |
| 1-Azabicyclo[2.2.2]octan-3-yl 2-Hydroxy-2-phenyl-3-pyrrolidinylpropionate dihydrochloride | 12230. | — | — | — |
| 1-Azabicyclo[2.2.2]octan-3-yl 2-hydroxy-3-(4-morpholinyl)-2-phenylpropionate | 195. | 0.08 | 49 | 0.63 |
| 1-Azabicyclo[2.2.2]octan-3-yl 2-Hydroxy-2-phenyl-3-(4-thiomorpholinyl)propionate | 158. | 0.07 | 46 | 0.1 |
| 1-Azabicyclo[2.2.2]octan-3-yl 3-(1,4-Dioxa-8 azospiro [4.5]-decanyl)-2-hydroxy-2-phenylpropionate | 5235 | — | 32.1 | — |
| 1-Azabicyclo[2.2.2]octan-3-yl 2-Hydroxy-2-phenyl-3-[4-(2,6-dimethylmorpholinyl)]-propionate dihydrochloride | — | — | 998 | 32.1 |

| Compd. | [³H]QNB Binding, Kb,nM | Colonic Motility Anesth. Rat, i.v., IC$_{50}$ (mg/kg) | Inhn. Carbachol-Stim. Cl- Sec. Kb,nM | Antag. Carbachol-ind. diarrhea, mice ip, ED$_{50}$, mg/lg |
|---|---|---|---|---|
| hemihydrate 1-Methyl-1-azabicyclo[2.2.2]octan-3-yl 2-Hydroxy-3-(4-morpholinyl)-2-phenyl-propionate Iodide | — | — | — | 14.0 |
| 1-Azabicyclo[2.2.2]octan-3-yl 2-Hydroxy-2-phenyl-3-piperazinyl-propionate trihydrochloride hydrate | — | — | — | — |

What is claimed is:

1. The invention provides novel compounds of formula:

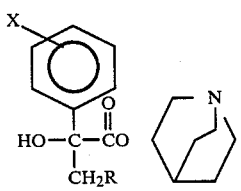

and their quaternary salts with lower alkyl halides, wherein:

X=H, halogen, lower alkyl, lower alkoxy, hydroxy, and

R=morpholinyl, thiomorpholinyl, piperidinyl, 1,4-dioxa-8-azaspiro[4.5]decanyl, 4-(2,6-dimethylmorpholinyl), 4-ketopiperidinyl, 4-hydroxypiperidinyl, 4-substituted piperazinyl (wherein the substituent is lower alkyl, hydroxyalkyl, acetoxyalkyl, or acyl).

2. The compound of claim 1 which is 1-azabicyclo[2.2.2]octan-3-yl 2-hydroxy-3-(4-morpholinyl)-2-phenylpropionate.

3. The compound of claim 1 which is 1-azabicyclo[2.2.2]octan-3-yl 2-hydroxy-2-phenyl-3-(4-thiomorpholinyl)propionate.

4. The compound of claim 1 which is 1-methyl-1-azabicyclo[2.2.2]octan-3-yl 2-hydroxy-3-(4-morpholinyl)-2-phenylpropionate iodide.

5. The compound of claim 1 which is 1-methyl-1-azabicyclo[2.2.2]octan-3-yl 2-hydroxy-2-phenyl-3-(4-thiomorpholinyl)propionate iodide.

6. A pharmaceutical composition comprising an effective amount of the compound of claim 1 and a pharmaceutically acceptable carrier.

7. A method for treating irritable bowel syndrome comprising administering to a host the composition of claim 6.

* * * * *